United States Patent [19]

Dye

[11] Patent Number: 5,496,323
[45] Date of Patent: Mar. 5, 1996

[54] ORTHOPEDIC INSTRUMENT WITH QUARTER-TURN DISCONNECT MECHANISM

[75] Inventor: Donald W. Dye, Pflugerville, Tex.

[73] Assignee: Intermedics Orthopedics, Inc., Austin, Tex.

[21] Appl. No.: 253,101

[22] Filed: Jun. 2, 1994

[51] Int. Cl.$^6$ .............................. A61B 17/56; B25G 3/00
[52] U.S. Cl. ..................... 606/79; 606/85; 403/325/348
[58] Field of Search ................................ 606/86, 79, 85, 606/84, 80, 99; 403/348, 349, 325, 321, 315; 16/114 R; 81/489, 479

[56] References Cited

U.S. PATENT DOCUMENTS 2,092,060  9/1937  Gairing ................................. 403/348
4,480,511  11/1984  Nickipuck ............................. 403/325
5,098,437  3/1992  Kashuba et al. ......................... 606/99

Primary Examiner—Tamara L. Graysay
Attorney, Agent, or Firm—John R. Merkling

[57] ABSTRACT

An orthopedic instrument having a quarter-turn disconnect apparatus. A female socket is provided on a broach or cutting instrument and a male plug with a locking mechanism is provided on a cutting apparatus. The male plug is inserted into the socket and pushed forward slightly against the resistance of a spring. The plug or socket are then turned one-quarter turn at which point the locking mechanism falls into place.

22 Claims, 3 Drawing Sheets

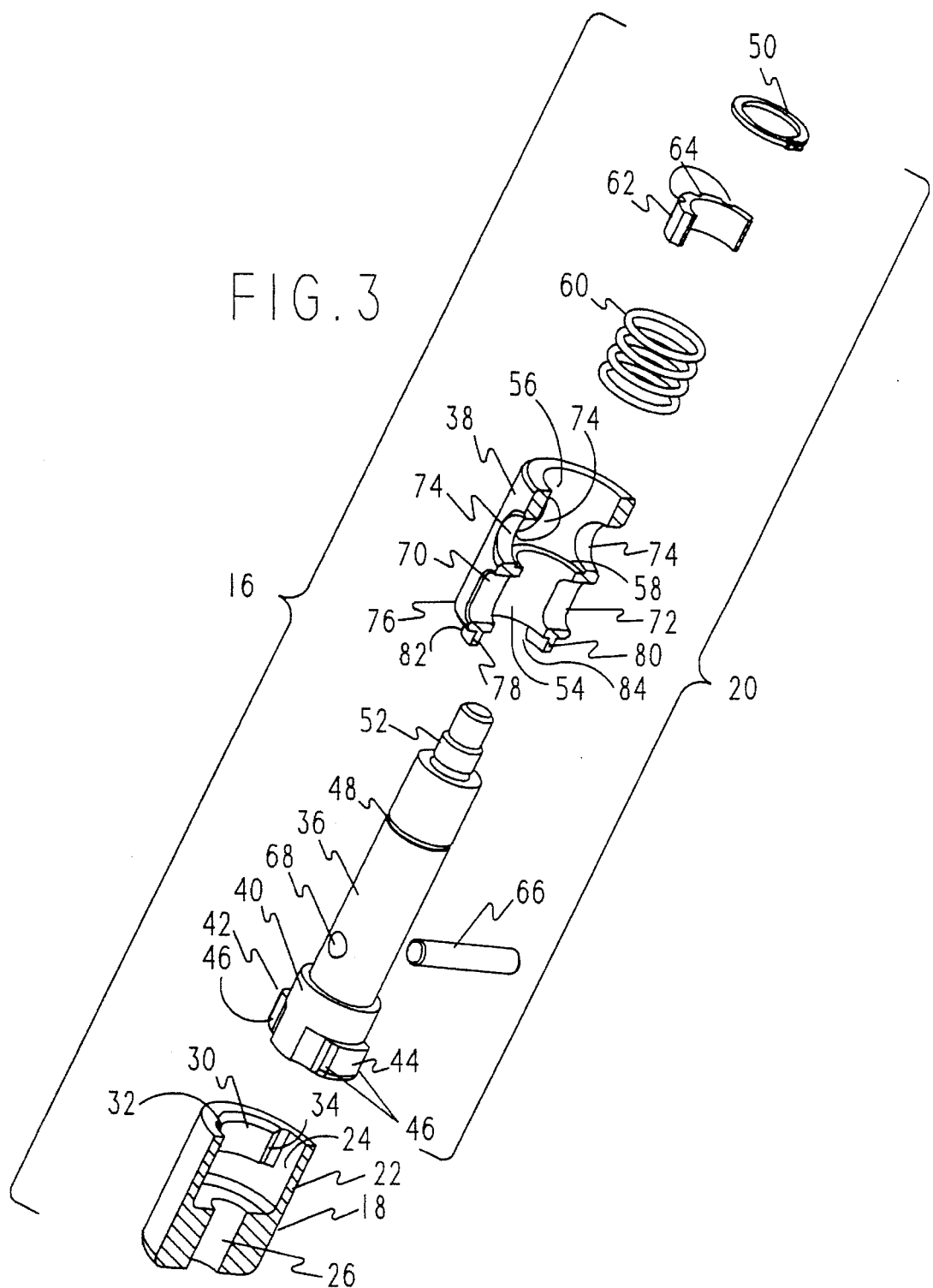

ORTHOPEDIC INSTRUMENT WITH QUARTER-TURN DISCONNECT MECHANISM

FIELD OF MY INVENTION

My invention relates to orthopedic instruments for use in orthopedic surgery.

BACKGROUND OF MY INVENTION

The field of orthopedic surgery comprises many different procedures for repairing damaged or defective bones and joints. To assist surgeons in accurately and replicably performing such procedures, numerous instruments have been proposed. In particular, cutting instruments, rasps and broaches are used to shape the bone and prepare the interior of the bone to receive prosthetic orthopedic implants such as prosthetic knees or hips. Such instruments may be driven by pneumatic hammer, or by a mechanical device known as a slap hammer. In many instances it is desirable to be able to exchange broaches or other instruments on the driving mechanism as different situations are encountered. The mechanism whereby the broach or other orthopedic instrument and the pneumatic hammer, slap hammer or other driving instrument are connected together needs to be easy to operate, reliable, mechanically robust and capable of sterilization.

SUMMARY OF MY INVENTION

I have invented an orthopedic instrument having a quarter-turn disconnect apparatus. In the specific embodiment shown, I have illustrated a slap hammer and orthopedic broach for preparing the proximal femur to receive an artificial hip implant. Those skilled in the art, however, will recognize that any orthopedic instrument could be substituted for the broach and any orthopedic driving mechanism could be substituted for the slap hammer. In the apparatus according to my invention a female socket is provided on the broach or cutting instrument and a male plug with a locking mechanism is provided on the cutting apparatus. The male plug is inserted into the socket by the surgeon and pushed forward slightly against the resistance of a spring. The plug or socket are then turned one-quarter turn at which point the locking mechanism falls into place. The apparatus is then completely secured.

With the foregoing in mind, therefore, it is an object of my invention to provide an orthopedic instrument with a quick disconnect feature.

It is a further object of my invention to provide such a quick disconnect apparatus which can be easily sterilized.

It is further object of my invention to provide a surgical instrument with a quick disconnect apparatus which can be securely and reliably locked in place.

These and other objects and features of my invention will be apparent to those skilled in the art from the following detailed description of my preferred embodiment taken with reprints to the accompanying drawing.

BRIEF DESCRIPTION OF THE DRAWINGS

1. FIG. I is a plan view of an orthopedic instrument according to my invention.

3. FIG. 3 is an exploded view of the quick disconnect of FIG. 2 with selected parts shown in partial section.

DETAILED DESCRIPTION OF MY PREFERRED EMBODIMENT

I will now explain my invention with reference to the drawings.

Figure 1:
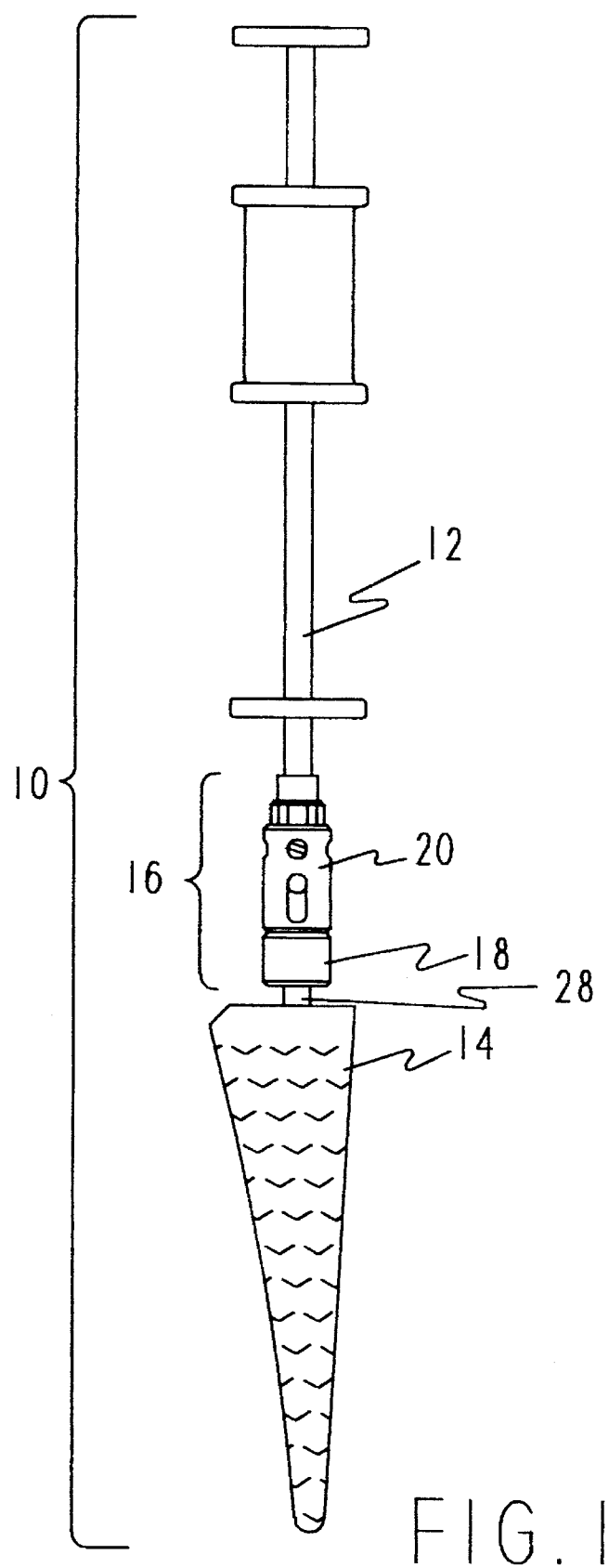

FIG. 1 shows a plan view of an orthopedic instrument 10 according to my invention. In the particular embodiment shown, the instrument 10 comprises a slap hammer 12 and orthopedic broach 14 with a quick disconnect mechanism 16 connecting the hammer 12 and the broach 14. Of course, any other driving mechanism, whether manual or mechanical, could be substituted for the hammer 12. Moreover, any cutting instrument or other orthopedic device could be substituted for the broach 14.

The quick disconnect 16 comprises a female socket 18, shown here mounted on the broach 14, and a male plug 20, shown here mounted on the hammer 12. The quick disconnect 16 can best be understood by reference to FIGS. 2 and 3.

Figure 2:
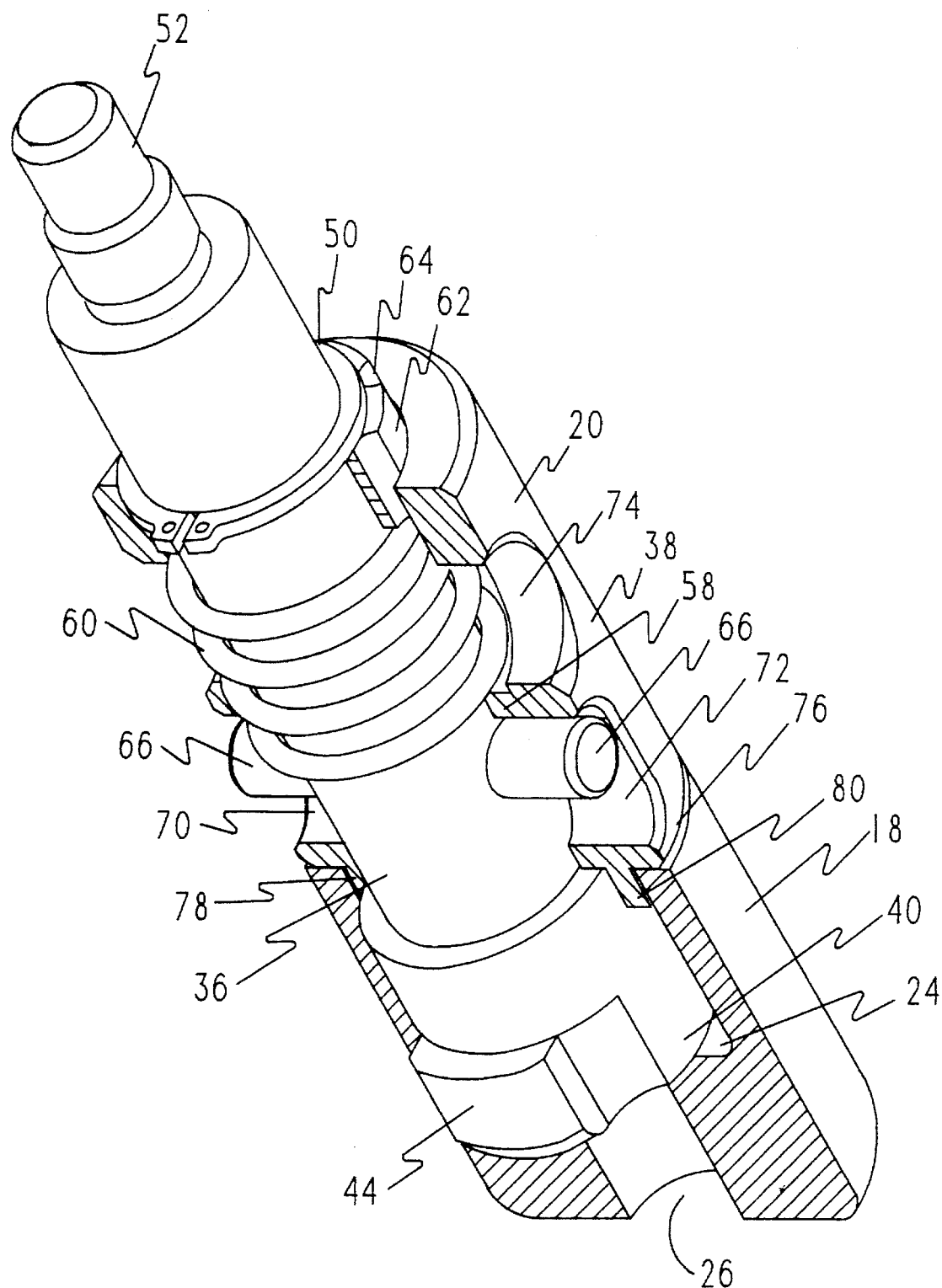
FIG. 2 is a perspective view of the quick disconnect mechanism according to my invention, in partial section.

In FIGS. 2 and 3, the femal socket 18 is shown in partial section. Where partial sections are shown, the half which not illustrated is the mirror image of the illustrated portion. The female socket 18 comprises a generally cylindrical body 22 having a proximal cavity 24. When used herein, proximal is intended to mean near the surgeon manipulating the device and distal is intended to mean remote from the surgeon. The socket 18 also has a distal through bore 26. This bore receives a shaft 28 or pin connected to the broach 14 in press fit relationship. These two parts may be secured in any convenient way, as far example by press fit, by welding or by threaded components. Within the proximal cavity 24 are two tabs 30, one of which can be seen in FIG. 3. As mentioned above, the tabs are mirror images of one another so that the description of one suffices for both. The tab 30 subtends approximately a 90° arc or less within the proximal cavity 24. It is relatively robust, having an axial length of approximately half the depth of the proximal cavity 24. The axial edges 32, 34 have a slight chamfer to facilitate engagement with the male plug 20.

The plug 20 comprises a shaft 36 with a locking sleeve 38. The shaft 36 has a distal end 40 which is sized to fit snugly into the proximal cavity 24 of the socket 18. As with the socket 18 the distal end 40 is provided with two opposed tabs 42, 44, which each subtends 90° of arc or a little less. The edges 46 of the tabs are also chamfered to facilitate assembly of the apparatus. The shaft 36 also has an annular groove 48 near its proximal end for receiving a split ring 50. A rod 52 shown at the proximal end of the shaft 36 represents a part of the driving apparatus or slap hammer 12 by which the male plug is attached to the driving apparatus.

The sleeve 38 comprises a hollow cylinder having a distal chamber 54 sized to fit slidingly around the shaft 36 and a slightly enlarged proximal chamber 56. The intersection of the two chambers 54, 56 forms a lip 58 upon which rides a compression spring 60. Proximal from the compression spring is a circumferential slide bearing 62, illustrated in partial section. The slide bearing 62 is long enough to permit axial displacement of the sleeve 38 without exposure of the spring 60. Axial grooves 64 in the slide bearing 62 permit penetration of sterilizing gasses. Axial movement of the sleeve 38 is limited by a pin 66 which is press fit into a through bore 68 in the shaft 36 and which engages opposed slots 70, 72 in the sleeve 38. These slots 70, 72 are shown in partial section in the figures. Circumferentially around the sleeve in the area of the upper chamber 56, I have provided a plurality of radial through bores 74 so that sterilizing gasses can easily penetrate into the spring and interior of the plug 20 during sterilization. At a distal edge 76 on the sleeve 38, two opposed axial tabs 78, 80 are provided. In the illustration, as mentioned heretofore, these tabs are shown in partial section and only half of the tab is illustrated, the other half being the mirror image of the illustrated part. The tabs 78, 80 extend distally in an axial direction from the sleeve. The ends 82, 84 of the tabs are chamfered.

I will now explain the operation of the quick disconnect according to my invention. In both FIG. 2 and FIG. 3, the orientation of the parts shown is for the locked condition of the quick disconnect. It will be noted that the sleeve 38 is restrained from turning about the shaft 36 by the pin 66 and can only move axially a distance limited by the slots 70, 72. To assemble the disconnect apparatus, the plug 20 is advanced toward socket 18, rotated at 90° clockwise or counter clockwise from its illustrated position. In such a situation, the tabs 42, 44 on the shaft 36 will not confront the tabs 30 on the socket 18, but rather will slide past those socket tabs. At the same time, however, the axial tabs 78, 80 on the sleeve 38 will encounter the socket tabs 30. As the plug 20 is pushed toward the socket 18, the spring 60 will be compressed, allowing the distal part 40 to be fully inserted into the proximal chamber 24 in the socket 18. The plug is then rotated 90° clockwise or counter clockwise until the axial tabs 78, 80 clear the socket tabs 30. The axial tabs 78, 80 then drop down between the socket tabs 30 locking the apparatus together. This condition is illustrated in FIG. 2.

To disassemble the apparatus, the sleeve 38 is pulled proximally until the axial tabs 78, 80 disengage the socket tabs 30. The plug can then be rotated 90° so that the tabs 42, 44 are no longer captured below the socket tabs 30 and the plug 20 can be withdrawn from the socket 18.

Those skilled in the art will recognize that my invention can be embodied in other specific forms without departing from the spirit or essential teaching thereof. The foregoing detailed description, therefore, is to be viewed in all respects as illustrative. The scope of my invention is to be defined by the appended claims.

I claim as my invention:

1. A surgical apparatus comprising
   means for manipulating the apparatus,
   means for affecting the body of a patient, and
   means for selectively connecting said manipulating means and said body affecting means, said manipulating means and said body affecting means being connected to said connecting means and said connecting means comprising
      plug means having
         a shaft connected to one of said manipulating means and said body affecting means, said shaft having at least one radially extending tab on a distal end thereof, said tab having an axial length and
         a sleeve slidingly mounted on said shaft, said sleeve having at least one axially extending tab on a distal end thereof, means for preventing rotation of said sleeve relative to said shaft and
      socket means connected to the other of said manipulating means and said body affecting means, said socket means having
         a proximal cavity for receiving said distal end of said shaft, said cavity having an axial depth, and
         at least one internal tab extending radially inwardly within said proximal cavity at a proximal end thereof and having an axial length less than said axial depth of said proximal cavity, said radially extending tab of said shaft being configured to seat axially beyond said internal tab and said axially extending tab of said sleeve being adapted to fit adjacent said internal tab and forming a means for inhibiting relative rotation of said plug means with respect to said socket means.

2. The surgical apparatus according to claim 1 wherein said plug means further comprise means for pushing said sleeve against said socket means.

3. The surgical apparatus according to claim 2 wherein said means for preventing rotation comprises at least one axial slot in said sleeve and at least one pin mounted on said shaft and extending into said axial slot and wherein said pushing means comprise a compression spring captured between said sleeve and said shaft.

4. The surgical apparatus according to claim 1 wherein said at least one radially extending tab on said shaft comprises a plurality of radially extending tabs, said at least one axially extending tab comprises a plurality of axially extending tabs and said at least one internal tab comprises a plurality of internal tabs.

5. The surgical apparatus according to claim 4 wherein said plurality of radially extending tabs comprise two radially extending tabs located substantially opposite each other across said shaft, said plurality of axially extending tabs comprise two axially extending tabs located substantially opposite each other across said shaft, and said plurality of internal tabs comprise two internal tabs located substantially opposite each other across said proximal cavity.

6. The surgical apparatus according to claim 5 wherein said plug means further comprise means for pushing said sleeve against said socket means.

7. The surgical apparatus according to claim 6 wherein said means for preventing rotation comprises at least one axial slot in said sleeve and at least one pin mounted on said shaft and extending into said axial slot and wherein said pushing means comprise a compression spring captured between said sleeve and said shaft.

8. The surgical apparatus according to claim 5 wherein said two radially extending tabs and said two axially extending tabs are spaced apart from each other circumferentially around said plug means.

9. The surgical apparatus according to claim 8 wherein said two internal tabs and said axially extending tabs, taken together, are adapted to substantially entirely circumscribe said shaft.

10. The surgical apparatus according to claim 9 wherein said plug means further comprise means for pushing said sleeve against said socket means.

11. The surgical apparatus according to claim 10 wherein said means for preventing rotation comprises at least one axial slot in said sleeve and at least one pin mounted on said shaft and extending into said axial slot and wherein said pushing means comprise a compression spring captured between said sleeve and said shaft.

12. An apparatus for connecting two surgical devices, said apparatus comprising
    plug means having
       a shaft for connection to one surgical device, said shaft having at least one radially extending tab on a distal end thereof, said tab having an axial length and
       a sleeve slidingly mounted on said shaft, said sleeve having at least one axially extending tab on a distal end thereof, means for preventing rotation of said sleeve relative to said shaft and socket means for connection to another surgical device, said socket means having a proximal cavity for receiving said distal end of said shaft, said cavity having an axial depth, and at least one internal tab extending radially inwardly within said proximal cavity at a proximal end thereof and having an axial length less than said axial depth of said proximal cavity, said radially extending tab of said shaft being configured to seat axially beyond said internal tab and said axially extending tab of said sleeve being adapted to fit adjacent said internal tab and forming a means for inhibiting relative rotation of said plug means with respect to said socket means.

13. The connecting apparatus according to claim 12 wherein said plug means further comprise means for pushing said sleeve against said socket means.

14. The connecting apparatus according to claim 13 wherein said means for preventing rotation comprises at least one axial slot in said sleeve and at least one pin mounted on said shaft and extending into said axial slot and wherein said pushing means comprise a compression spring captured between said sleeve and said shaft.

15. The connecting apparatus according to claim 12 wherein said at least one radially extending tab on said shaft comprises a plurality of radially extending tabs, said at least one axially extending tab comprises a plurality of axially extending tabs and said at least one internal tab comprises a plurality of internal tabs.

16. The connecting apparatus according to claim 15 wherein said plurality of radially extending tabs comprise two radially extending tabs located substantially opposite each other across said shaft, said plurality of axially extending tabs comprise two axially extending tabs located substantially opposite each other across said shaft, and said plurality of internal tabs comprise two internal tabs located substantially opposite each other across said proximal cavity.

17. The connecting apparatus according to claim 16 wherein said plug means further comprise means for pushing said sleeve against said socket means.

18. The connecting apparatus according to claim 17 wherein said means for preventing rotation comprises at least one axial slot in said sleeve and at least one pin mounted on said shaft and extending into said axial slot and wherein said pushing means comprise a compression spring captured between said sleeve and said shaft.

19. The connecting apparatus according to claim 16 wherein said two radially extending tabs and said two axially extending tabs are spaced apart from each other circumferentially around said plug means.

20. The connecting apparatus according to claim 19 wherein said two internal tabs and said axially extending tabs, taken together, are adapted to substantially entirely circumscribe said shaft.

21. The connecting apparatus according to claim 20 wherein said plug means further comprise means for pushing said sleeve against said socket means.

22. The connecting apparatus according to claim 21 wherein said means for preventing rotation comprises at least one axial slot in said sleeve and at least one pin mounted on said shaft and extending into said axial slot and wherein said pushing means comprise a compression spring captured between said sleeve and said shaft.

\* \* \* \* \*